(12) United States Patent
Vermeulen et al.

(10) Patent No.: US 10,010,250 B2
(45) Date of Patent: Jul. 3, 2018

(54) DENTAL APPARATUS AND METHOD OF UTILIZING THE SAME

(71) Applicant: KONINKLIJKE PHILIPS N.V., Eindhoven (NL)

(72) Inventors: Olaf Thomas Johan Antonie Vermeulen, Oss (NL); Steven Charles Deane, Cambridge (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 217 days.

(21) Appl. No.: 14/442,140

(22) PCT Filed: Dec. 17, 2013

(86) PCT No.: PCT/IB2013/061019
§ 371 (c)(1),
(2) Date: May 12, 2015

(87) PCT Pub. No.: WO2014/097135
PCT Pub. Date: Jun. 26, 2014

(65) Prior Publication Data
US 2016/0287084 A1    Oct. 6, 2016

Related U.S. Application Data

(60) Provisional application No. 61/739,415, filed on Dec. 19, 2012.

(51) Int. Cl.
*A61B 5/00* (2006.01)
*A61C 17/22* (2006.01)
(Continued)

(52) U.S. Cl.
CPC .......... *A61B 5/0088* (2013.01); *A61B 5/0071* (2013.01); *A61B 5/4547* (2013.01);
(Continued)

(58) Field of Classification Search
CPC ....... A61B 5/0088; A61B 1/24; A61B 5/0071; A61B 5/0095; A61B 1/00006;
(Continued)

(56) References Cited

U.S. PATENT DOCUMENTS 4,290,433 A * 9/1981 Alfano ................. A61B 5/0088
356/237.1
4,479,499 A * 10/1984 Alfano ................. A61B 5/0088
356/317

(Continued)

FOREIGN PATENT DOCUMENTS

CN        1309545 A    8/2001
CN        1671320 A    9/2005
(Continued)

OTHER PUBLICATIONS

Gerritsen et al: "Fluorescence Lifetime Imaging of Oxygen in Dental Biofilm"; Proceedings of SPIE, vol. 4164, Jan. 2000, pp. 70-78.

(Continued)

*Primary Examiner* — Nicholas Lucchesi
*Assistant Examiner* — Shannel Wright

(57) ABSTRACT

A dental apparatus is provided. The dental apparatus include a handle. A controller operably couples to the housing. A subsystem is in operable communication with the controller and configured to generate an excitation signal causing an emitted fluorescence light to be reflected back to the subsystem and to the controller for analyzing one or more properties of the emitted fluorescence light. The one or more properties corresponding to a decay time of the emitted fluorescence light, wherein plaque emitted florescence light decays faster than tooth emitted florescence light. The controller is programmed to analyze detected emitted fluorescence light to determine if the emitted fluorescence light is indicative of a plaque emitted fluorescence decay time or (Continued)

tooth emitted florescence light decay time to detect the presence of one of dental plaque and tooth demineralization.

25 Claims, 5 Drawing Sheets

(51) Int. Cl.
  *A61C 17/34* (2006.01)
  *A61B 1/04* (2006.01)
(52) U.S. Cl.
  CPC .......... *A61B 5/7257* (2013.01); *A61C 17/225* (2013.01); *A61C 17/34* (2013.01); *A61B 1/043* (2013.01); *A61B 2560/0223* (2013.01)
(58) Field of Classification Search
  CPC ............ A61B 1/043; A61B 2560/0223; A61C 17/225; A61C 17/34
  See application file for complete search history.

(56) References Cited

U.S. PATENT DOCUMENTS

| | | | | |
|---|---|---|---|---|
| 5,382,163 A * | 1/1995 | Putnam | ................. | A61C 19/04 433/215 |
| 5,894,620 A * | 4/1999 | Polaert | ................. | A61B 5/0088 15/22.1 |
| 5,957,687 A * | 9/1999 | Brilliant | ............... | A61B 5/0079 433/31 |
| 6,024,562 A * | 2/2000 | Hibst | ................... | A61B 5/0088 433/29 |
| 6,053,731 A * | 4/2000 | Heckenberger | ...... | A61B 5/0088 433/29 |
| 6,179,611 B1 * | 1/2001 | Everett | ............... | A61B 5/0088 433/29 |
| 6,186,780 B1 * | 2/2001 | Hibst | ................... | A61B 5/0088 433/215 |
| 6,272,376 B1 * | 8/2001 | Marcu | ................ | G01N 21/6486 600/477 |
| 6,485,300 B1 * | 11/2002 | Muller | ............... | A46B 15/0002 433/29 |
| 6,561,802 B2 * | 5/2003 | Alexander | ........... | A61B 5/0088 433/29 |
| 6,862,771 B1 * | 3/2005 | Muller | ............... | A46B 15/0002 15/105 |
| 6,902,397 B2 * | 6/2005 | Farrell | ................. | B08B 7/0057 15/167.1 |
| 7,862,335 B2 * | 1/2011 | Berube-Lauziere | . | A61B 5/0088 433/29 |
| 7,955,076 B2 * | 6/2011 | Yamagishi | .......... | A61B 5/0088 433/29 |
| 8,027,709 B2 * | 9/2011 | Arnone | ................ | A61B 5/0088 433/29 |
| 8,187,002 B2 * | 5/2012 | Reddy | ................. | A61B 5/0071 128/898 |
| 8,314,377 B2 * | 11/2012 | Binner | ................. | A61B 1/0646 15/167.1 |
| 8,360,771 B2 * | 1/2013 | Stookey | ............ | A61B 1/00041 433/29 |
| 8,512,040 B2 * | 8/2013 | Binner | ................ | A46B 15/0002 128/898 |
| 8,721,327 B2 * | 5/2014 | Karazivan | ........... | A61B 5/0088 433/29 |
| 9,517,015 B2 * | 12/2016 | Deane | ................. | A61B 5/0088 |
| 9,723,993 B2 * | 8/2017 | Vermeulen | ........... | A61B 5/0071 |
| 2004/0106081 A1 * | 6/2004 | Karazivan | ............ | A61B 5/0088 433/29 |
| 2005/0170316 A1 * | 8/2005 | Russell | .............. | A46B 15/0002 433/216 |
| 2006/0047190 A1 * | 3/2006 | Jenkins | ................ | A61B 5/0088 600/340 |
| 2006/0141421 A1 * | 6/2006 | Braunecker | .......... | A61B 5/0088 433/215 |
| 2007/0111166 A1 * | 5/2007 | Dursi | ................. | A46B 15/0002 433/215 |
| 2007/0111167 A1 * | 5/2007 | Russell | .............. | A46B 15/0002 433/216 |
| 2007/0156037 A1 * | 7/2007 | Pilon | .................... | A61B 5/0059 600/310 |
| 2007/0280888 A1 * | 12/2007 | Fujikawa | ........... | A46B 15/0044 424/9.71 |
| 2008/0024779 A1 * | 1/2008 | Aasmul | ................ | G01J 3/4406 356/317 |
| 2008/0060148 A1 * | 3/2008 | Pinyayev | ............. | A61B 5/0088 15/22.1 |
| 2008/0082000 A1 * | 4/2008 | Thoms | ............... | A61B 1/00177 600/476 |
| 2011/0151409 A1 * | 6/2011 | Binner | ................ | A61B 1/0646 433/215 |
| 2011/0240057 A1 | 10/2011 | Lorch | | |
| 2011/0314618 A1 * | 12/2011 | Binner | ............... | A46B 15/0002 15/22.1 |
| 2011/0318713 A1 * | 12/2011 | Binner | ................ | A61C 17/221 433/216 |
| 2012/0123399 A1 * | 5/2012 | Belikov | ............... | A61B 18/201 606/16 |
| 2012/0326055 A1 * | 12/2012 | Wilson | ................ | A61B 5/0059 250/459.1 |
| 2013/0203008 A1 * | 8/2013 | Kressman | .......... | A46B 15/0034 433/27 |
| 2015/0283401 A1 * | 10/2015 | Cha | .................... | A46B 15/0036 433/29 |

FOREIGN PATENT DOCUMENTS

| | | | | |
|---|---|---|---|---|
| CN | 102028555 A | | 4/2011 | |
| EP | 2526852 A1 * | 11/2012 | ......... | A61B 1/00057 |
| WO | 9959462 A1 | | 11/1999 | |
| WO | 2004012593 A1 | | 2/2004 | |

OTHER PUBLICATIONS

Heinrich-Weltzien et al: "Quantitativee Light-Induced Fluorescence (QLF)—A Potential Method for the Dental Practitioner"; Restorative Dentistry, Quintessence International, vol. 34, No. 3, Mar. 2003, pp. 181-188.
De Oliveira et al: "Time-Resolved Fluoresence Spectroscopy of White-Spot Caries in Human Enamal"; Applied Optics, Optical Society of America, vol. 49, No. 12, pp. 2244-2249.
Koenig et al: "Laser-Induced Autofluorescence for Medical Diagnosis"; Journal of Fluorescence, vol. 4, No. 1, 1994, pp. 17-40.
Borisova et al: "Early Differentation Between Caries and Tooth Demineralization Using Laser-Induced Autofluorescence Spectroscopy"; Lasers in Surgery and Medicine, 34:249-253, 2004.
Sun et a: "High Speed Multi-Frequency Impedance Analysis of Single Particles in a Microfluidic Cytometer Using Maximum Length Sequences"; Lap Chip, 2007, vol. 7, pp. 1034-1040.
Lakowicz: "Principles of Fluorescence Spectroscopy" 2nd Edition, Kluwer Academic/Plenum, 1999; ISBN 10-0-306-46093-9.

* cited by examiner

DENTAL APPARATUS AND METHOD OF UTILIZING THE SAME

CROSS-REFERENCE TO PRIOR APPLICATIONS

This application is the U.S. National Phase application under 35 U.S.C. § 371 of International Application No. PCT/IB2013/061019, filed on Dec. 17, 2013, which claims the benefit of U.S. Provisional Patent Application No. 61/739,415, filed on Dec. 19, 2012. These applications are hereby incorporated by reference herein.

BACKGROUND

Technical Field

The present disclosure relates to a dental apparatus and method of utilizing the same. More particularly, the present disclosure relates to a dental apparatus and method of use of the dental apparatus utilizing a frequency modulated excitation signal causing an emitted fluorescence light that is analyzed to detect dental plaque.

Description of Related Art

It is desirable to detect plaque deposits in the oral cavity to direct action for removal, for example by using toothbrushes (manual or power), tooth floss, tooth picks, or oral irrigators, as detection indicates the areas at which dental cleaning effort should be focused. Such deposits can be difficult to detect in situ/in vivo on the teeth, gums, tongue, or cheek. It is especially important to detect dental plaque. For detection of dental plaque it is known to use fluorescence measurement, in which incident radiation is directed at the surfaces of the oral cavity, and fluorescence radiation having characteristics associated with the presence of biological deposits is emitted from the surfaces and is detected.

In the state of the art there are two general methods for detecting dental plaque. One method uses primary fluorescence, where the fluorescence of dental plaque or other dental material itself is monitored. The other method uses secondary fluorescence, where surfaces in the oral cavity suspected of bearing dental plaque are treated with a fluorescent label material which preferentially binds to dental plaque, and the fluorescence emission of the label material on the oral cavity surfaces to which it has bound is detected to indicate the presence of dental plaque.

In accordance with the foregoing, apparatuses configured for detecting dental plaque sometimes utilizes monochromatic light to illuminate a potential dental plaque site. In certain instances, the site may be illuminated by a light having a predetermined wavelength or range. Other methods and/or apparatuses may utilize a fast excitation pulse (e.g., nanosecond or faster) and fast and sensitive detection devices that are enabled (e.g., gated) at very short time intervals after the excitation pulse. Such methods and/or apparatuses, typically, utilize photomultiplier tubes, avalanche photodiodes and/or Kerr-gates.

While the aforementioned methods and apparatuses are suitable for detecting dental plaque, such methods and apparatuses are generally expensive and include components that are, typically, bulky and require high voltages.

SUMMARY

As can be appreciated, a dental apparatus and method of use of the dental apparatus utilizing a frequency modulated excitation signal causing an emitted fluorescence light that is analyzed to detect dental plaque may prove useful in dentistry.

An aspect of the instant disclosure provides a dental apparatus. The dental apparatus include a handle. A controller operably couples to the housing. A subsystem is in operable communication with the controller and configured to generate an excitation signal causing an emitted fluorescence light to be reflected back to the subsystem and to the controller for analyzing one or more properties of the emitted fluorescence light. The one or more properties corresponding to a decay time of the emitted fluorescence light, wherein plaque emitted florescence light decays faster than tooth emitted florescence light. The controller is programmed to analyze detected emitted fluorescence light to determine if the emitted fluorescence light is indicative of a plaque emitted fluorescence light decay time or tooth emitted florescence light decay time to detect the presence of one of dental plaque and tooth demineralization.

The excitation signal may be frequency modulated and provided on a single frequency and/or multiple frequencies. The subsystem may include a light emitting diode, a laser diode, a filter, a photodetector, an imaging sensor, an amplifier, an oscillator, a mixer, and an analog to digital converter. The filter may be an optical excitation cleanup filter, and the oscillator may be a single or multi-frequency modulated oscillator and the beam-splitter may be a dichroic beamsplitter. The subsystem may be configured to detect emitted fluorescence light in a frequency that ranges from about 10 Hz to about 10 GHz. A calibration module may be in operable communication with the controller for calibrating out phase delays and frequency dependent gains associated with a tooth of a patient.

A battery may be housed within the handle and configured to supply power to the dental apparatus including a motor that is housed within the handle and the subsystem, which is housed in a shaft that extends distally from handle. A toothbrush assembly may be configured to releasably couple to the shaft for brushing teeth and removing the dental plaque. A window may be positioned on the toothbrush assembly adjacent a plurality of bristles provided thereon. Moreover, the window may align with the subsystem disposed on the shaft such that the excitation signal and the emitted fluorescence light are passable through the window.

The one or more properties of the emitted fluorescence light may be a phase shift associated with the emitted fluorescence light and amplitude of the emitted fluorescence light. The controller may include one or more control algorithms that are configured to analyze the phase shift of the emitted fluorescence light and/or the amplitude of the emitted fluorescence light and/or the time decay properties of the fluorescence light. Time domain and frequency domain analysis methods may be utilized by the control algorithm(s) to determine the phase shift and amplitude of the emitted fluorescence light.

An aspect of the instant disclosure provides a dental apparatus. The dental apparatus includes a handle including a shaft extending distally therefrom, and a battery, motor and controller housed therein. A toothbrush assembly is configured to removably couple to the shaft. The subsystem is in operable communication with the controller and configured to generate a frequency or time modulated excitation signal causing an emitted fluorescence light to be reflected back to the subsystem and the controller for analyzing one or more properties of the emitted fluorescence light. The one or more properties correspond to a decay time of the emitted fluorescence light, wherein plaque emitted florescence light decays faster than tooth emitted florescence light. The controller is programmed to analyze detected emitted fluorescence light to determine if the emitted fluorescence light is indicative of a plaque emitted fluorescence light decay time or tooth emitted florescence light decay time to detect the presence of one of dental plaque and tooth demineralization.

The frequency modulated excitation signal may be provided on a single frequency and/or multiple frequencies. The subsystem may include a light emitting diode, a laser diode, a VCSEL, a filter, a photodetector, an imaging sensor, an amplifier, an oscillator, a mixer, a beam-splitter and an analog to digital converter. The filter may be an optical fluorescence excitation cleanup filter, the oscillator may be a single or multi-frequency modulated oscillator and the beam-splitter may be a dichroic beam-splitter. The subsystem may be configured to detect emitted fluorescence light in a frequency that ranges from about 10 Hz to about 10 GHz. A calibration module may be in operable communication with the controller for calibrating out phase delays and frequency dependent gains associated with a tooth of a patient.

A window may be positioned on the toothbrush assembly adjacent a plurality of bristles provided thereon. Moreover, the window may align with the subsystem disposed on the shaft such that the excitation signal and the emitted fluorescence light are passable through the window.

The one or more properties of the emitted fluorescence light may be a phase shift associated with the emitted fluorescence light and amplitude of the emitted fluorescence light. The controller may include one or more control algorithms that are configured to analyze the phase shift of the emitted fluorescence light and the amplitude of the emitted fluorescence light. Time domain and frequency domain analysis methods may be utilized by the control algorithm(s) to determine the phase shift and amplitude of the emitted fluorescence light.

An aspect of the instant disclosure provides a method for detecting one of dental plaque and tooth demineralization at a site on a tooth. A frequency modulated excitation signal is, initially, emitted inside a mouth of a patient. Thereafter, an emitted fluorescence light is detected. One or more properties of the emitted fluorescence light are analyzed to detect the presence of dental plaque, wherein plaque emitted florescence light decays faster than tooth emitted florescence light. And, the detected emitted fluorescence light is analyzed to determine if the emitted fluorescence light is indicative of a plaque emitted fluorescence light decay time or tooth emitted florescence light decay time to detect the presence of one of dental plaque and tooth demineralization.

The excitation signal may be frequency modulated on a single frequency and/or multiple frequencies. Emitted fluorescence light may be detected in a frequency that ranges from about 10 Hz to about 10 GHz. Phase shift and amplitude properties of the emitted fluorescence light may be analyzed. Time domain and frequency domain analysis methods may be utilized to analyze the phase shift and amplitude of the emitted fluorescence light.

A dental apparatus may be provided for emitting, detecting and analyzing. The dental apparatus may be provided with a handle including a battery that is configured to supply power to the dental apparatus including a motor that is housed within the handle, a controller and subsystem, which is housed in a shaft that extends distally from handle.

The subsystem may include a light emitting diode, a laser diode, a filter, a photodetector, an imaging sensor, an amplifier, an oscillator, a mixer, a beam-splitter and an analog to digital converter. An optical fluorescence excitation cleanup filter, a single or multi-frequency modulated oscillator and a dichroic beam-splitter may be utilized. Phase delays and frequency dependent gains associated with the tooth may be calibrated out via a calibration module that is in operable communication with the controller.

A toothbrush assembly that is configured to releasably couple to the shaft for brushing teeth and/or removing the dental plaque may be provided. A window that is positioned on the toothbrush assembly adjacent a plurality of bristles may be provided on the toothbrush assembly. The window may be aligned with the subsystem disposed on the shaft such that the excitation signal and the emitted fluorescence light are passable through the window.

BRIEF DESCRIPTION OF THE DRAWINGS

The aspects of the present disclosure may be better understood with reference to the following figures. The components in the figures are not necessarily to scale, emphasis instead being placed upon clearly illustrating the principles of the disclosure. Moreover, in the figures, like reference numerals designate corresponding parts throughout the several views.

In the figures.

DETAILED DESCRIPTION

The present disclosure describes various embodiments of apparatuses and methods that utilize one or more power levels of excitation light for detecting one or more tooth anomalies such that the tooth anomalies may be removed. Specifically, a dental apparatus, e.g. an electric toothbrush, is configured to provide a frequency modulated excitation light that is configured to cause an emitted fluorescence light to be reflected back to the dental apparatus for analyzing one or more parameters of the emitted fluorescence that correspond to a decay time of the emitted fluorescence light. The one or more parameters are, subsequently, utilized to detect the presence of a tooth anomaly, e.g., dental plaque, tooth enamel demineralization, dental caries, etc. When the dental plaque is detected, the dental apparatus may then be utilized to remove the dental plaque.

Figures 1A, 1B:
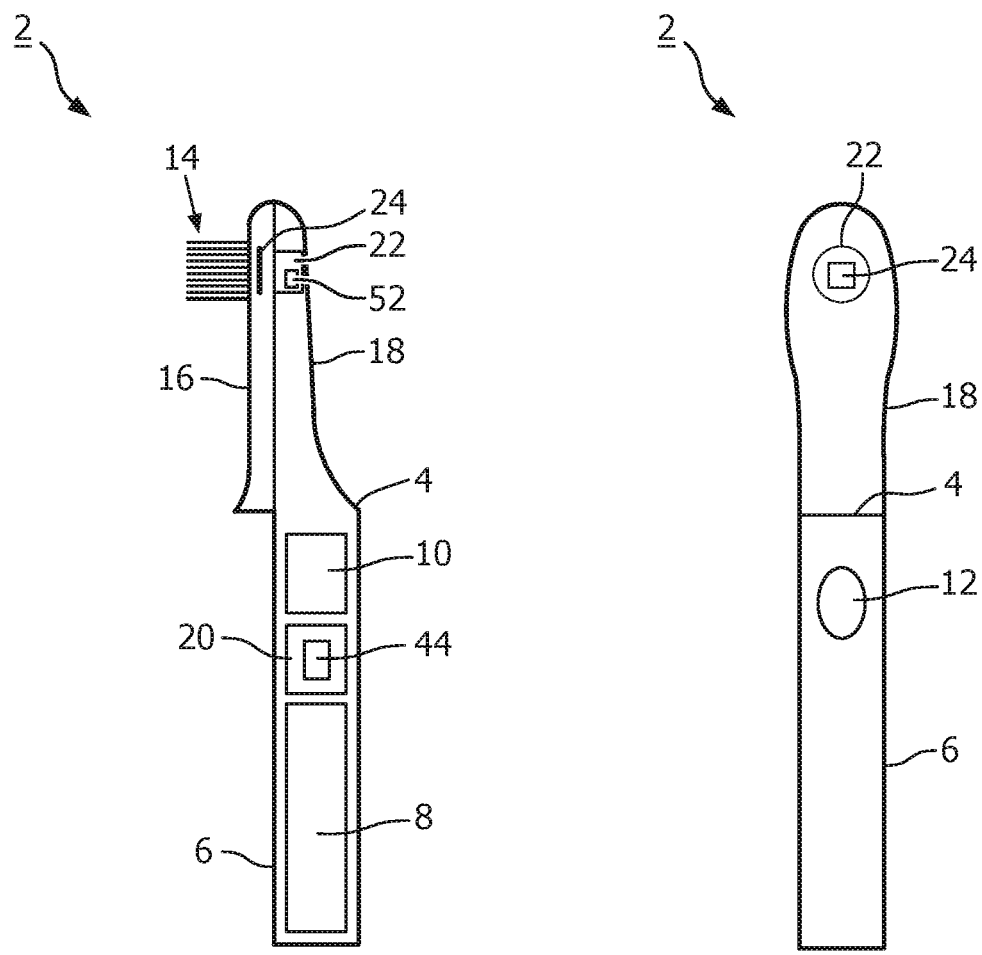
FIGS. 1A and 1B are front and side views, respectively, of a dental apparatus according to an embodiment of the instant disclosure.

FIG. 1A illustrates a system 2 that is configured to detect dental plaque. System 2 may be configured for use with a variety of handheld dental implements. In the illustrated embodiment, system 2 is in the form of a multipurpose dental apparatus 4 (e.g., a combination electric toothbrush and dental plaque detector). Dental apparatus 4 includes a handle 6 of suitable configuration that is configured to house a battery 8 and an electric motor 10. A power button or switch 12 (FIG. 1B) is provided on the handle 6 and operably couples to battery 8 for supplying power to dental apparatus 4 and components operably associated therewith, e.g., electric motor 10, a controller 20, etc., when depressed. A plurality of bristles 14 of suitable configuration is provided on toothbrush assembly 16 that is configured to detachably couple via one or more coupling methods, e.g., clips (not explicitly shown), to a shaft 18 that extends distally from handle 6.

Figure 2:
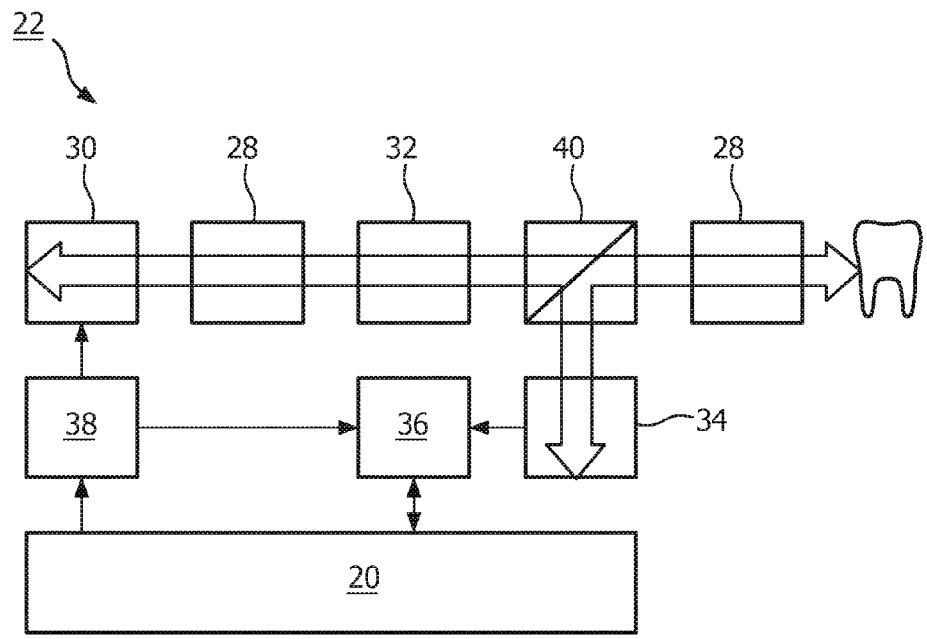
FIG. 2 is block diagram illustrating a controller and subsystem of the dental apparatus shown in FIGS. 1A and 1B.

FIG. 2 is block diagram illustrating an embodiment of a controller 20 and subsystem 22 that may be provided with dental apparatus 4. Subsystem 22 may include any suitable electrical and/or non-electrical components that are capable of generating, emitting and/or detecting various power intensities and wavelengths of frequency modulated excitation light, e.g. blue light, red light etc. Subsystem 22 may include, without limitation, for example, one or more light sources 30, photodetectors 34, lock-in amplifier 36, oscillators 38, beam splitters 40, and optical components 28.

Light sources 30 may be any suitable light source. In the embodiment illustrated in FIG. 2, light source 30 is in the form of one or more light emitting diodes 30, e.g., a plurality of light emitting diodes 30 (LEDs 30). LEDs 30 may be configured to generate or emit one or more suitable wavelengths of light. In accordance with the instant disclosure, for example, it is has been found that light having wavelengths of 405 nm, 440 nm, 470 nm and/or 480 nm (all visible light, e.g., blue light) were suitable for the purposes described herein. Specifically, light in the visible light spectrum was chosen due to the safety concerns of using other wavelengths of light, e.g., ultraviolet light, infrared, etc., in the mouth, and the cost typically attributed with utilizing such wavelengths of light. Other light sources, e.g. diode laser, and different wavelengths may also be utilized.

Photodetectors 34 are configured to detect the presence of dental plaque on tooth enamel. Specifically, photodetectors 34 are configured and utilized to detect emitted fluorescence associated with tooth material and/or with dental plaque and convert detected emitted fluorescence photons into an electrical signal that is sent to a controller 20 for processing, described in greater detail below.

In accordance with the instant disclosure, photodetectors 34 may be configured to detect emitted fluorescence associated with tooth material and/or with dental plaque in a frequency that ranges from about 10 Hz to about 10 GHz. In one particular embodiment, for example, the frequency may range from about 1 MHz to about 10 GHz. In another embodiment, the frequency may range from about 10 Hz to about 100 MHz; this particular embodiment may be utilized to optimize signal to noise related to emitted fluorescence decay characteristics of tooth material. Alternatively, in embodiments, image sensors (not explicitly shown) may be utilized in place of photodetectors 34. In this particular embodiment, image processing may be utilized to convert pixel intensities into a form that can be used to determine when dental plaque has been detected. While photodetectors 34 and the image sensors are both suitable for detecting the aforementioned emitted fluorescence associated with tooth material and/or dental plaque, the simplicity of photodetectors 34 makes them ideal for the purposes described herein. As can be appreciated, dental apparatus 4 may include a combination of photodetectors 34 and imaging sensors.

In order to shield photodetectors 34 from various wavelengths of excitation light and/or unwanted background radiation, optical filters (not explicitly shown) may be mounted onto photodetectors 34. Additionally, the photodetectors 34 may include one or more collection and focusing optics such as, for example, lenses, compound parabolic concentrators or a combination of both.

Beam-splitter 40 is utilized to direct frequency modulated excitation light towards teeth and reflect the emitted fluorescence light, which has a longer wavelength, towards photodetectors 34. Accordingly, a dichroic beam splitter which has a short-pass characteristic was utilized for this purpose. Alternatively, instead of using beam splitter 40, we can use two optical paths, one for excitation and one for detection; this may be advantageous in certain embodiments, e.g., to accommodate design variations of dental apparatus 4.

An optional filter 32 may be provided and utilized to block any undesired wavelengths (e.g. ultraviolet light) of light from reaching the teeth or the photodetectors 34. In the illustrated embodiments, for example, filter 32 is a narrow bandpass filter. Filter 32 may be arranged in other configurations to accommodate different wavelengths and/or power intensities of light and/or to achieve different filtering outcomes.

Oscillator 38 may be any suitable oscillator. In the illustrated embodiment, oscillator 38 is operably coupled to LEDs 30 and configured to drive LEDs 30 such that LEDs 30 generate or emit a frequency modulated excitation light or signal. The frequency modulated excitation signal may be emitted at a single frequency or multi-frequencies simultaneously; the latter may be implemented as multiple discrete frequencies (or mixed together) and used to discriminate against potentially interfering materials in a mouth of a user, e.g., composite fillings.

Lock-in amplifier 36 is configured to receive input signals from oscillator 38 and photodetectors 34 and outputs a corresponding signal that corresponds to the detected emitted fluorescence to controller 20. Specifically, oscillator 38 provides a reference frequency (e.g., the frequency of the frequency modulated excitation signal) to lock-in amplifier 36. Lock-in amplifier 36 utilizes this reference frequency to filter out the unwanted portions, e.g., noise, of the signal received from photodetectors 34 and communicates the remaining portions of the signal that is required for processing to controller 20. In essence, lock-in amplifier 36 functions as a phase sensitive detector. As can be appreciated, other amplifiers and/or signal processing devices may be utilized for the purposes described herein.

Subsystem 22 is configured to illuminate tooth material (and in some instances gums) from the frequency modulate excitation signal emitted through toothbrush assembly 16 adjacent to where plurality of bristles 14 are disposed. With this purpose in mind, an optical window 24 (FIGS. 1A and 1B) of suitable of configuration is provided on toothbrush assembly 16 adjacent plurality of bristles 14 and is configured to allow light to pass therethrough for detection thereof by subsystem 22. Specifically, when toothbrush assembly 16 is coupled to shaft 18, window 24 aligns with subsystem 22 including LEDs 30, photodetectors 34, amplifiers 36, oscillators 38, beam splitters 40, and optical components 28 such that the frequency modulated excitation signal generated from LEDs 30 is emitted through window 24 and reflected light (e.g., emitted fluorescence of tooth material and/or dental plaque) is transmitted back through window 24 and detected by photodetectors 34.

With reference again to FIG. 1A, dental apparatus 4 includes controller 20 (e.g., a microprocessor) that communicates with subsystem 22 (as best seen in FIG. 2) that is configured to generate, emit and detect light, e.g., frequency modulated excitation signal and emitted fluorescence associated with tooth material and dental plaque. Controller 20 can be a processor, microcontroller, a system on chip (SOC), field programmable gate array (FPGA), etc. Collectively the one or more components, which can include a processor, microcontroller, SOC, and/or FPGA, for performing the various functions and operations described herein are part of a controller 20, as recited, for example, in the claims. Controller 20 can be provided as a single integrated circuit (IC) chip which can be mounted on a single printed circuit board (PCB). Alternatively, the various circuit components of controller 20, including, for example, the processor, microcontroller, etc. are provided as one or more integrated circuit chips. That is, the various circuit components may be located on one or more integrated circuit chips.

Controller 20 communicates with subsystem 22 and is configured to analyze one or more properties of the emitted fluorescence light. In the illustrated embodiment, the one or more properties of the emitted fluorescence light may be phase shift associated with the emitted fluorescence light and/or amplitude of the emitted fluorescence light.

In accordance with the instant disclosure, the phase shift (and/or amplitude) is correlated to a decay time of the emitted fluorescence light and utilized to detect the presence of dental plaque. Specifically, through empirical testing it has been found that there is a direct correlation between a phase shift (and/or amplitude) of detected emitted fluorescence light and fluorescence decay times. More specifically, it is known that emitted fluorescence from a tooth without dental plaque on a surface thereof decays more slowly when compared to emitted fluorescence from a tooth with dental plaque, i.e., a tooth with dental plaque decays faster. Accordingly, detected emitted fluorescence of a tooth with dental plaque will have a lower phase shift at a specific frequency range when compared to a phase shift of detected fluorescence of a tooth without dental plaque. At low frequencies, for example, the phase shift will be zero for both cases, e.g., tooth with/without dental plaque. At very high frequencies both situations will show 90 degrees of phase shift. At frequencies between these two extremes, the phase shift of clean enamel/dentine will be greater than that of the enamel/dentine covered with plaque. In other words: A faster decay time (time domain) means a lower phase shift in the frequency domain. A similar correlation can be made with respect to amplitude of the detected emitted fluorescence. The demodulation of the fluorescence light of a clean enamel/dentin site will be greater at a specific modulation frequency than the demodulation of the fluorescence light of the same site covered with dental plaque. In accordance with the foregoing, controller 20 includes one or more control algorithms that are configured to analyze a phase shift (and/or amplitude) of the emitted fluorescence light utilizing time domain and/or frequency domain analysis methods. The control algorithm may utilize one or more transforms to calculate the phase shift (and/or amplitude). For example, Discrete Fourier Transform (DFT), Fast Fourier Transform (FFT) and/or Laplace Transform may be utilized to calculate the phase shift and/or amplitude of the detected emitted fluorescence.

Figure 4:
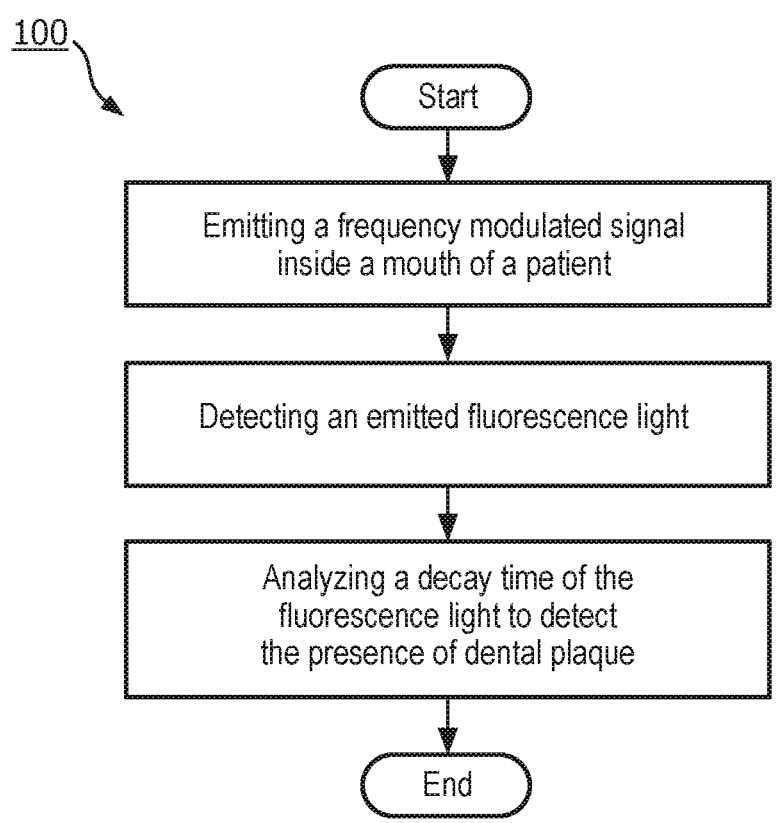
FIG. 4 is a flow chart illustrating a method of detecting dental plaque.

Operation of system 2 is described in terms of a method 100 for detecting dental plaque in the frequency domain. Dental apparatus 4 may, initially, be positioned within a mouth of a user. When the dental apparatus 4 is powered on, plurality of bristles 14 are rotated, in conventional fashion, and a frequency modulated excitation signal is emitted from LEDs 30 (see FIG. 4 at step 102) which causes an emitted fluorescence light to be reflected back to photodetectors 34 (see FIG. 4 at step 104).

Thereafter, controller 20 receives an output signal from lock-in amplifier 36. The control algorithm utilizes one or more of the aforementioned transforms to calculate the phase shift (and/or amplitude) of the detected emitted fluorescence. Controller 20 utilizes a closed loop feedback loop to continuously monitor the presence of a phase shift of the detected emitted fluorescence to ensure that all dental plaque is removed from a tooth site. In embodiments, dental apparatus 4 may be equipped with one or more indicating devices, e.g., audio, visual, etc. (not explicitly shown), that are configured to give a user an indication when a specific site on the tooth is clean. After such an indication, a user can then move to a different site on the tooth or the next tooth. As can be appreciated, this may reduce the overall brushing time of user and/or may also lead to a better, more conscious brushing routine.

The aforementioned process repeats to continuously measure a level of dental plaque on the current tooth being brushed. Dental apparatus 4 can communicate the presence of dental plaque to the user in a wide variety of ways e.g. by illuminating one more LEDS on handle 8 (not explicitly shown).

Dental apparatus 4 helps a user clean their teeth while informing the user if they are removing dental plaque from their teeth and if they have fully removed the dental plaque. Moreover, dental apparatus 4 provides information regarding dental plaque in real time during brushing. Dental apparatus 4 accomplishes the foregoing, without the use of the aforementioned bulky, expensive components that utilize high voltage and that are typically associated with convention dental plaque apparatuses.

From the foregoing and with reference to the various figure drawings, those skilled in the art will appreciate that certain modifications can also be made to the present disclosure without departing from the scope of the same. For example, in some embodiments, subsystem 22 may be built into handle 8 to allow shaft 18 to be replaced. In this instance, frequency modulated excitation signals may be delivered to toothbrush assembly 16 and emitted fluorescence light reflected back to photodetectors 34 and controller 20 via optical fibers (not explicitly shown). Moreover, in this embodiment, one or more light guides (not explicitly shown) may be provided on dental apparatus 4 and configured to channel light to and from window 24.

Figure 3:
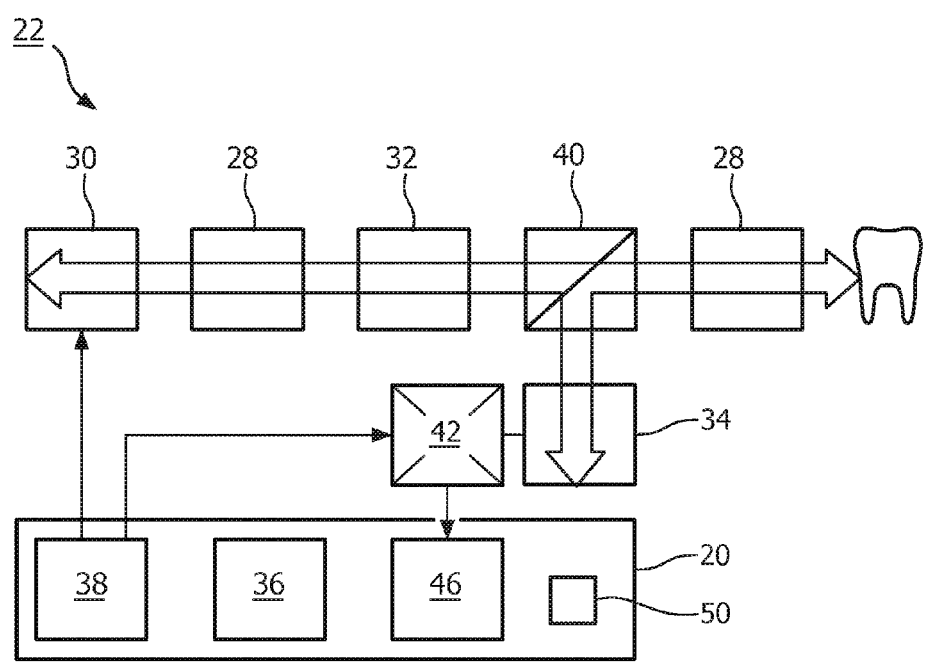
FIG. 3 is block diagram illustrating a controller and subsystem of a dental apparatus according to another embodiment of the instant disclosure.

In the embodiment illustrated in FIG. 2, controller 20 and subsystem 22 are configured to function in an analogue domain. In embodiments (see FIG. 3 for example), however, oscillator 38 and/or lock-in amplifier 36 can be implemented in a digital domain. In this particular embodiment, digital implementation may be included into controller 20, e.g., an analog heterodyning stage, to down convert signals to an intermediate frequency band better suited for analog-to-digital conversion. Specifically, for each frequency modulated excitation signal, oscillator 38 (a digital oscillator for example) generates a frequency modulated excitation signal with a small offset for a mixer 42 that outputs fall in a frequency range of an analog-to-digital converter 46. Thereafter, all remaining signal processing is done digitally and in accordance with the above.

Moreover, in the instance where a large number of fluorescence measurements are needed, oscillator 38 and LEDs 30 may be configured to generate and emit a maximum length sequence, which would allow detection of fluorescence over a large number of frequencies simultaneously. In this instance, controller 20 may include one or more analogue to digital converters 46 and a suitable digital processing unit (not explicitly shown) configured to extract the separate frequency responses and/or transform the separate frequency responses into an impulse response.

Further, while the aforementioned dental apparatus 4 has been described utilizing frequency domain calculations to achieve the above-referenced outcomes, it is within the purview of the instant disclosure to utilize time domain calculations to achieve the above referenced outcomes. As can be appreciated in this instance, one or more modifications may be made to dental apparatus 4 and/or components operably associated therewith. For example, in this particular embodiment, light-source(s) 30 may be pulsed.

As is known, there is a certain variation in lifetime decay data of human enamel. Although the aforementioned dental apparatus 4 does not rely on determination of the actual decay-times, variations of actual decay-times may limit the useful signal range. Accordingly, it may prove useful to calibrate dental apparatus 4 on a clean piece of tooth material for each user individual. To this end, a calibration module 44 (FIG. 1A) may be in operable communication with controller 20 and configured to calibrate dental apparatus 4. As can be appreciated, this may maximize a signal range. Specifically, by calibrating out all phase delays and frequency dependent gains on a clean tooth, the aforementioned analysis will provided a more accurate measure of the amount of dental plaque detected.

As noted above, the dental apparatus 4 can also be utilized to detect other tooth anomalies. For example, and with specific reference to FIG. 5, the measurement results in a polar plot of tooth enamel from different samples at 45.43 MHz, e.g., bovine tooth enamel, human tooth enamel and a human enamel sample affected by demineralization is illustrated. Specifically, the detected fluorescence properties are plotted as M sin ($\Phi$) versus M cos ($\Phi$) (e.g., the 90° phase shifted component vs. in-phase part of the response). In accordance with the instant disclosure, a phase angle, which is an angle between the x-axis and the location at a given frequency and the distance from the origin, provides a magnitude of the response.

Figure 6:
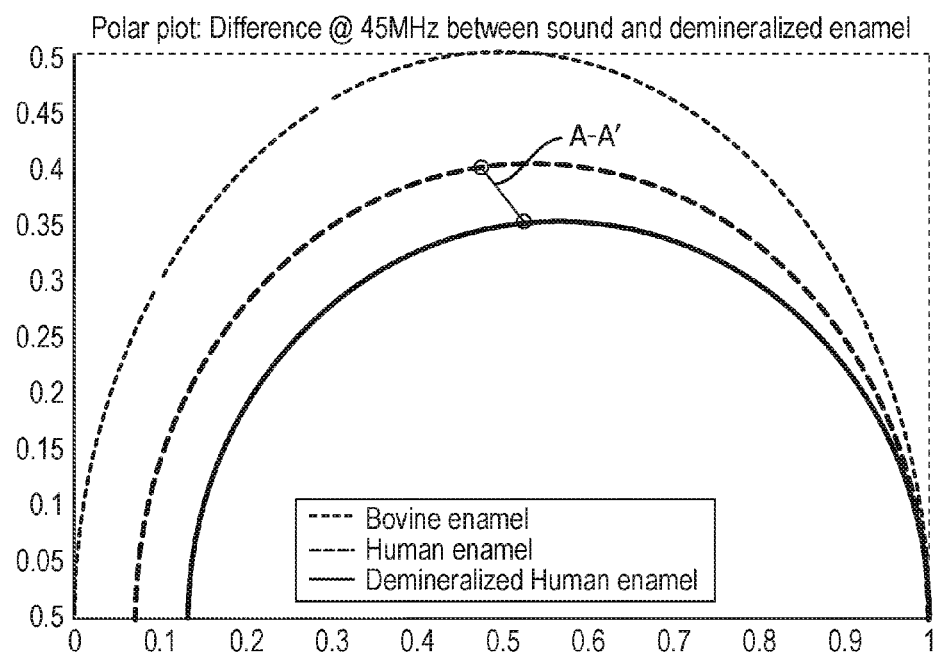
FIG. 6 is a graph of sound enamel and demineralized enamel showing the difference vector between both at a modulation frequency of 45 MHz.

In accordance with the instant disclosure, data relating to a signal corresponding to a sound tooth (e.g., a first reference signal) and a signal corresponding to a tooth affected by demineralization (e.g., a second reference signal) was plotted as a polar plot to illustrate a difference in these signals at a particular frequency (FIG. 6). In accordance with the instant disclosure, the polar plot is utilized to extract the presence of demineralized enamel from the frequency domain fluorescence data. Specifically, a plot of M sin ($\Phi$) versus M cos ($\Phi$) (e.g., the 90° phase shifted component vs. in-phase part of the response), where M is the normalized emission modulation and $\Phi$ is the phase delay of the fluorescence emission with respect to an excitation signal. As evident from this graph, a measurement at a single (or a limited number of modulation frequencies) is enough to detect the presence of a white spot lesion, e.g., demineralization.

FIG. 6 shows a demineralization affected tooth and a tooth with no demineralization, i.e., a tooth with a sound surface, and allows a prediction of were a tooth with partial demineralization may lie on along the line A-A'; with low demineralization coverage being near the sound tooth location. Thus, a measure of the degree of demineralization is possible, provided the end points of the line A-A' are known.

In accordance with the instant disclosure, the full frequency domain data was analyzed to determine the optimum modulation frequency. Specifically, and with reference to FIG. 7, the optimum modulation frequency was determined to be in the range from about 25 MHz to 100 MHz. With this data and the data obtained from FIGS. 5 and 6, it is evident that the presence of a white spot lesion can be based on the distance from a single modulation frequency result (e.g., in, but not limited to, the range of 25 MHz to 100 MHz) to the corresponding frequency point in the sound enamel locus.

Figure 5:
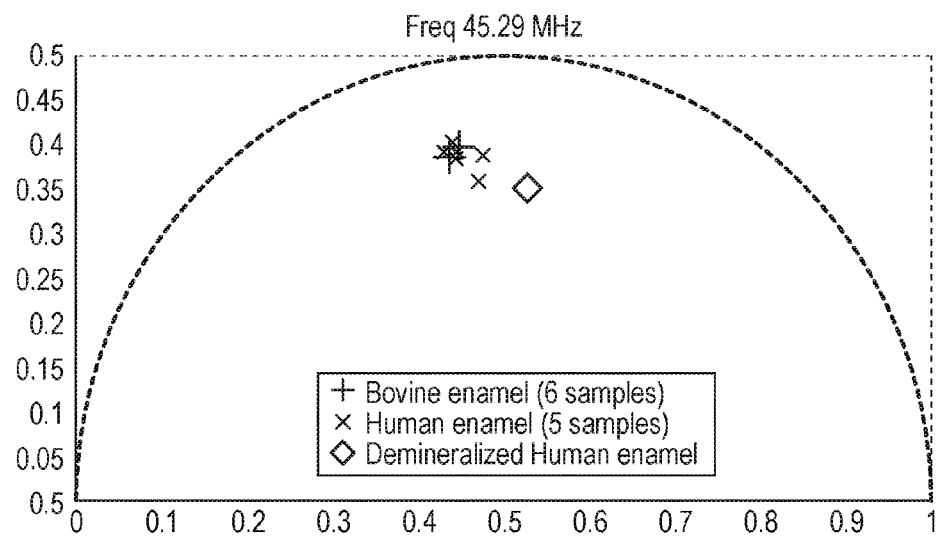
FIG. 5 is a graph of measurements taken from different samples of teeth illustrating variability of tooth enamel associated with the different samples and demineralized human enamel.
Figure 7:
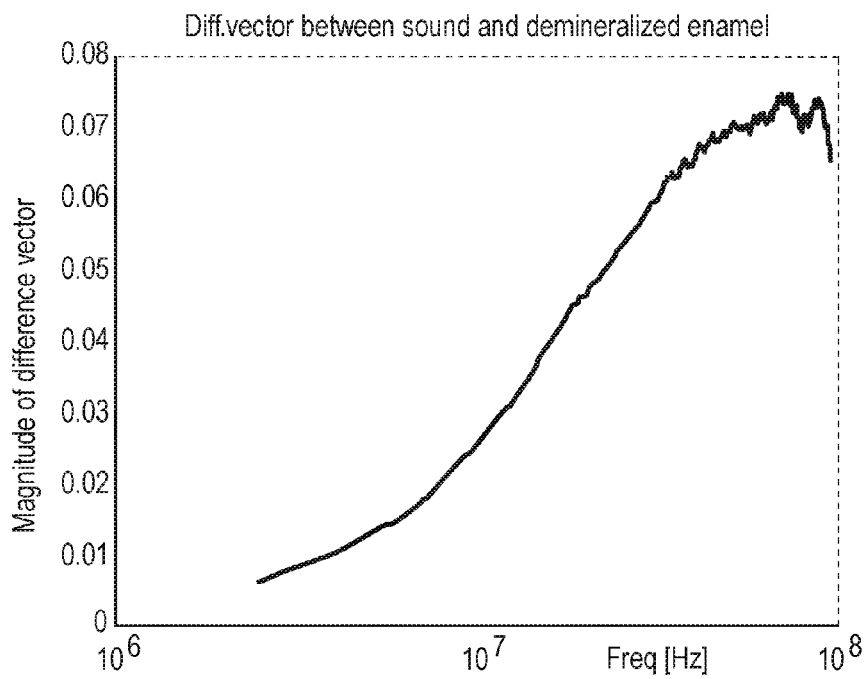
FIG. 7 is a graph of the difference vector between sound enamel and demineralized enamel.

As can be appreciated, the data collected from FIGS. 5-7 can also be correlated to a tooth covered with dental plaque.

Operation of system 2 is described in terms of a method 200 for detecting dental caries and/or demineralization. The dental apparatus 4 may, initially, be positioned within a mouth of a user.

Figure 8:
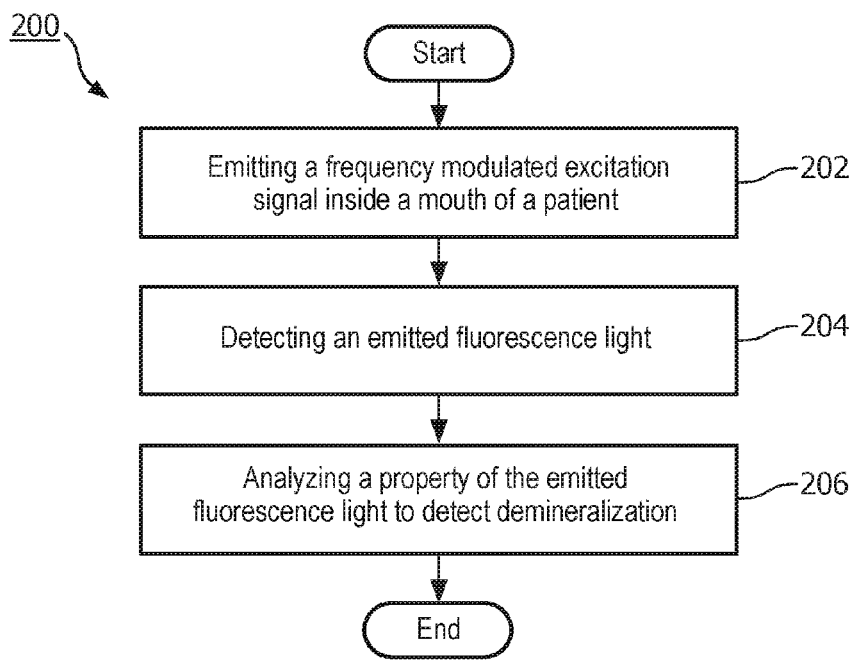
FIG. 8 is a flow chart illustrating a method of detecting demineralization and/or dental caries according to an embodiment of the present disclosure.

Thereafter, the plurality of bristles 14 are activated and rotated, in conventional fashion, and a frequency modulated excitation signal is emitted from LEDs 30 which causes an emitted fluorescence light to be reflected back to photodetectors 34 (see FIG. 8 at step 202); this can be accomplished on a tooth covered with toothpaste foam or free from toothpaste foam.

Thereafter, controller 20 receives an output signal from lock-in amplifier 36. The control algorithm utilizes one or more of the aforementioned transforms to calculate the phase shift (and/or amplitude) of the detected emitted fluorescence (see FIG. 8 at steps 204 and 206). The controller 20 utilizes a closed loop feedback loop to continuously monitor the presence of a phase shift of the detected emitted fluorescence to detect white spot lesions associated with demineralization at a tooth site.

In embodiments, dental apparatus 4 may be equipped with one or more indicating devices, e.g., audio, visual, etc. (not explicitly shown), that are configured to give a user an indication of dental caries and/or at the onset demineralization.

The aforementioned process repeats to continuously measure a level of dental caries and/or demineralization on the current tooth being brushed. Dental apparatus 4 can communicate the presence of dental caries and/or demineralization to the user in a wide variety of ways e.g. by illuminating the aforementioned one more LEDS that may be provided on the handle 8.

Dental apparatus 4 provides information regarding dental caries and/or demineralization in real time during brushing. Additionally, in the event that demineralization is detected, a user may begin a fluoride regiment (or other suitable regiment) to begin remineralization of a tooth, which, in turn, can restore the tooth with sound enamel. The dental apparatus 4 accomplishes the foregoing, without the use of the aforementioned bulky, expensive components that utilize high voltage and that are typically associated with conventional dental caries and/or demineralization apparatuses.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A dental apparatus, comprising:
   a handle;
   a controller operably coupled to the handle; and
   a subsystem in operable communication with the controller and configured to generate a frequency modulated excitation signal causing an emitted fluorescence light to be reflected back from a user's teeth based on a fluorescence of teeth and/or plaque to the subsystem and to the controller for analyzing a decay time of the emitted fluorescence light, wherein plaque emitted fluorescence light decays faster than tooth emitted fluorescence light,
   wherein the controller is programmed to analyze detected emitted fluorescence light to determine if the emitted fluorescence light is indicative of a plaque emitted fluorescence light decay time or tooth emitted fluorescence light decay time to detect the presence of dental plaque, wherein the controller is further configured to analyze a phase shift of the emitted fluorescence light or an amplitude of the emitted fluorescence light utilizing at least one of frequency domain analysis and time domain analysis methods.

2. The dental apparatus according to claim 1, wherein the frequency modulated excitation signal is provided on a single frequency or multiple frequencies.

3. The dental apparatus according to claim 1, wherein the subsystem includes at least one of a light emitting diode, a laser diode, a filter, a photodetector, an imaging sensor, an amplifier, an oscillator, a mixer, a beam-splitter or an analog to digital converter.

4. The dental apparatus according to claim 3, wherein the filter is an excitation cleanup filter, the oscillator is a single or multi-frequency modulated oscillator and the beam-splitter is a dichroic beam-splitter.

5. The dental apparatus according to claim 1, wherein the subsystem is configured to detect emitted fluorescence light in a frequency that ranges from about 10 Hz to about 10 GHz.

6. The dental apparatus according to claim 5, further including a calibration module that is in operable communication with the controller for calibrating out phase delays and frequency dependent gains associated with a tooth of a patient.

7. The dental apparatus according to claim 1, wherein a battery is housed within the handle and is configured to supply power to the dental apparatus including a motor housed within the handle and the subsystem housed in a shaft that extends distally from handle.

8. The dental apparatus according to claim 1, further including a toothbrush assembly that is configured to releasably couple to a shaft for at least brushing teeth and removing the dental plaque.

9. The dental apparatus according to claim 8, wherein a window is positioned on the toothbrush assembly adjacent a plurality of bristles provided thereon and aligns with the subsystem disposed on the shaft, such that the excitation signal and the emitted fluorescence light are passable through the window.

10. A dental apparatus, comprising:
    a handle including a shaft extending distally therefrom and a battery, motor and controller housed therein;
    a toothbrush assembly configured to removably couple to the shaft and a subsystem in operable communication with the controller and configured to generate one of a frequency and time modulated excitation signal causing an emitted fluorescence light to be reflected back from a user's teeth based on a fluorescence of teeth and/or plaque to the subsystem and the controller for analyzing a decay time of the emitted fluorescence light, wherein plaque emitted fluorescence light decays faster than tooth emitted fluorescence light,
    wherein the controller is programmed to analyze detected emitted fluorescence light to determine if the emitted fluorescence light is indicative of a plaque emitted fluorescence light decay time or tooth emitted fluorescence light decay time to detect the presence of dental plaque, wherein the controller is further configured to analyze a phase shift of the emitted fluorescence light or an amplitude of the emitted fluorescence light utilizing at least one of frequency domain analysis and time domain analysis methods.

11. The dental apparatus according to claim 10, wherein the frequency modulated excitation signal is provided on a single frequency or multiple frequencies.

12. The dental apparatus according to claim 10, wherein the subsystem includes at least one of a light emitting diode, a laser diode, a filter, a photodetector, an imaging sensor, an amplifier, an oscillator, a mixer, a beam-splitter or an analog to digital converter.

13. The dental apparatus according to claim 12, wherein the filter is an excitation cleanup filter, the oscillator is a single or multi-frequency modulated oscillator and the beam-splitter is a dichroic beam-splitter.

14. The dental apparatus according to claim 10, wherein the subsystem is configured to detect emitted fluorescence light in a frequency that ranges from about 10 Hz to about 10 GHz.

15. The dental apparatus according to claim 14, further including a calibration module that is in operable communication with the controller for calibrating out phase delays and frequency dependent gains associated with a tooth of a patient.

16. The dental apparatus according to claim 10, wherein a window is positioned on the toothbrush assembly adjacent a plurality of bristles provided thereon and aligns with the subsystem disposed on the shaft such that the excitation signal and the emitted fluorescence light are passable through the window.

17. A method for detecting one of dental plaque and tooth demineralization at a site on a tooth, comprising:
    emitting a frequency modulated excitation signal inside a mouth of a patient;
    detecting an emitted fluorescence light from a user's teeth based on a fluorescence of teeth and/or plaque; and
    analyzing at least one property of the emitted fluorescence light, wherein plaque emitted fluorescence light decays faster than tooth emitted fluorescence light; and
    analyzing detected emitted fluorescence light to determine if the emitted fluorescence light is indicative of a plaque emitted fluorescence light decay time or tooth emitted fluorescence light decay time to detect the presence of dental plaque, wherein the step of analyzing detected emitted fluorescence light further includes analyzing a phase shift or amplitude of the emitted fluorescence light utilizing frequency domain analysis methods to analyze the phase shift or amplitude of the emitted fluorescence light.

18. The method according to claim 17, including frequency modulating the excitation signal on a single frequency or multiple frequencies.

19. The method according to claim 17, including detecting the emitted fluorescence light in a frequency that ranges from about 10 Hz to about 10 GHz.

20. The method according to claim 17, including providing a dental apparatus for emitting, detecting and analyzing, and providing the dental apparatus with a handle including a battery that is configured to supply power to the dental apparatus including a motor housed within the handle and subsystem housed in a shaft that extends distally from handle.

21. The method according to claim 20, including providing the subsystem with at least one of a light emitting diode, a laser diode, a filter, a photodetector, an imaging sensor, an amplifier, an oscillator, a mixer, a beam-splitter or an analog to digital converter.

22. The method according to claim 21, including utilizing an optical excitation cleanup filter, a single or multi-frequency modulated oscillator and a dichroic beam-splitter.

23. The method according to claim 17, including calibrating out phase delays and frequency dependent gains associated with the tooth via a calibration module that is in operable communication with a controller.

24. The method according to claim 17, including providing a toothbrush assembly that is configured to releasably couple to the shaft for at least brushing teeth and removing the dental plaque.

25. The method according to claim 24, including providing the dental apparatus with a window that is positioned on the toothbrush assembly adjacent a plurality of bristles provided thereon and aligns with the subsystem disposed on the shaft such that the excitation signal and the emitted fluorescence light are passable through the window.

* * * * *